United States Patent
Barrus et al.

(10) Patent No.: US 11,096,727 B2
(45) Date of Patent: Aug. 24, 2021

(54) MODULAR SPINAL FIXATION DEVICE

(71) Applicant: K2M, Inc., Leesburg, VA (US)

(72) Inventors: Michael Barrus, Redondo Beach, CA (US); Brandon Moore, Leesburg, VA (US)

(73) Assignee: K2M, Inc., Leesburg, VA (US)

( * ) Notice: Subject to any disclaimer, the term of this patent is extended or adjusted under 35 U.S.C. 154(b) by 145 days.

(21) Appl. No.: 16/478,944

(22) PCT Filed: Jan. 18, 2018

(86) PCT No.: PCT/US2018/014179
§ 371 (c)(1),
(2) Date: Jul. 18, 2019

(87) PCT Pub. No.: WO2018/136602
PCT Pub. Date: Jul. 26, 2018

(65) Prior Publication Data
US 2020/0038075 A1 Feb. 6, 2020

Related U.S. Application Data

(60) Provisional application No. 62/487,516, filed on Apr. 20, 2017, provisional application No. 62/447,515, filed on Jan. 18, 2017.

(51) Int. Cl.
*A61B 17/70* (2006.01)
*A61B 17/72* (2006.01)

(52) U.S. Cl.
CPC ...... *A61B 17/7241* (2013.01); *A61B 17/7037* (2013.01); *A61B 17/7091* (2013.01); *A61B 17/7082* (2013.01)

(58) Field of Classification Search
CPC ............ A61B 17/7241; A61B 17/7037; A61B 17/7091; A61B 17/702; A61B 17/7035;
(Continued)

(56) References Cited

U.S. PATENT DOCUMENTS 9,277,938 B2 * 3/2016 Biedermann ...... A61B 17/8605
9,393,048 B2 7/2016 Carbone et al.
(Continued)

FOREIGN PATENT DOCUMENTS

EP 2277466 A1 1/2011

OTHER PUBLICATIONS

International Search Report from Application No. PCT/US2018/014179 dated Apr. 30, 2018, 2 pages.
(Continued)

*Primary Examiner* — Pedro Philogene
(74) *Attorney, Agent, or Firm* — Lerner, David, Littenberg, Krumholz & Mentlik, LLP

(57) ABSTRACT

A spinal fixation device is provided including a modular head assembly and a bone screw. The modular had assembly includes a housing, an anvil, an insert, and a snap ring. The housing defines a proximal surface and an opposite, distal surface, and the proximal and distal surfaces define a throughbore therethrough. The anvil is configured to be slidably received within a portion of the throughbore. The insert defines a proximal surface and an opposite, distal surface, and the distal surface defines a first counterbore therein that terminates at a first annular surface. The first annular surface defines a second counterbore that terminates at a second annular surface. The snap ring is configured to be disposed within the first counterbore of the insert when in a first configuration, and within the second counterbore of the insert when in a second configuration.

19 Claims, 13 Drawing Sheets

(58) Field of Classification Search
CPC .............. A61B 17/8615; A61B 17/863; A61B 17/8605; A61B 17/7004; A61B 17/864; A61B 17/7038; A61B 17/7008; A61B 17/7076; A61B 17/7055; A61B 17/705; A61B 17/704; A61B 17/7031; A61B 17/7086; A61B 17/8625; A61B 17/8685
See application file for complete search history.

(56) References Cited

U.S. PATENT DOCUMENTS

| | | | |
|---|---|---|---|
| 10,363,073 B2 * | 7/2019 | Raina | A61B 17/7007 |
| 2002/0026193 A1 | 2/2002 | Barker et al. | |
| 2004/0097933 A1 | 5/2004 | Lourdel et al. | |
| 2008/0004625 A1 * | 1/2008 | Runco | A61B 17/7037 |
| | | | 606/273 |
| 2011/0098755 A1 | 4/2011 | Jackson et al. | |
| 2013/0046345 A1 | 2/2013 | Jones et al. | |
| 2013/0345754 A1 | 12/2013 | Doubler et al. | |
| 2014/0243900 A1 | 8/2014 | Ark et al. | |
| 2015/0119940 A1 | 4/2015 | Jackson et al. | |
| 2015/0142059 A1 * | 5/2015 | Biedermann | A61B 17/7035 |
| | | | 606/266 |
| 2016/0262801 A1 | 9/2016 | Rezach et al. | |
| 2016/0331413 A1 | 11/2016 | Daniels | |

OTHER PUBLICATIONS

Extended European Search Report for EP18742380.1 dated Jun. 16, 2020; 3 pages.

* cited by examiner

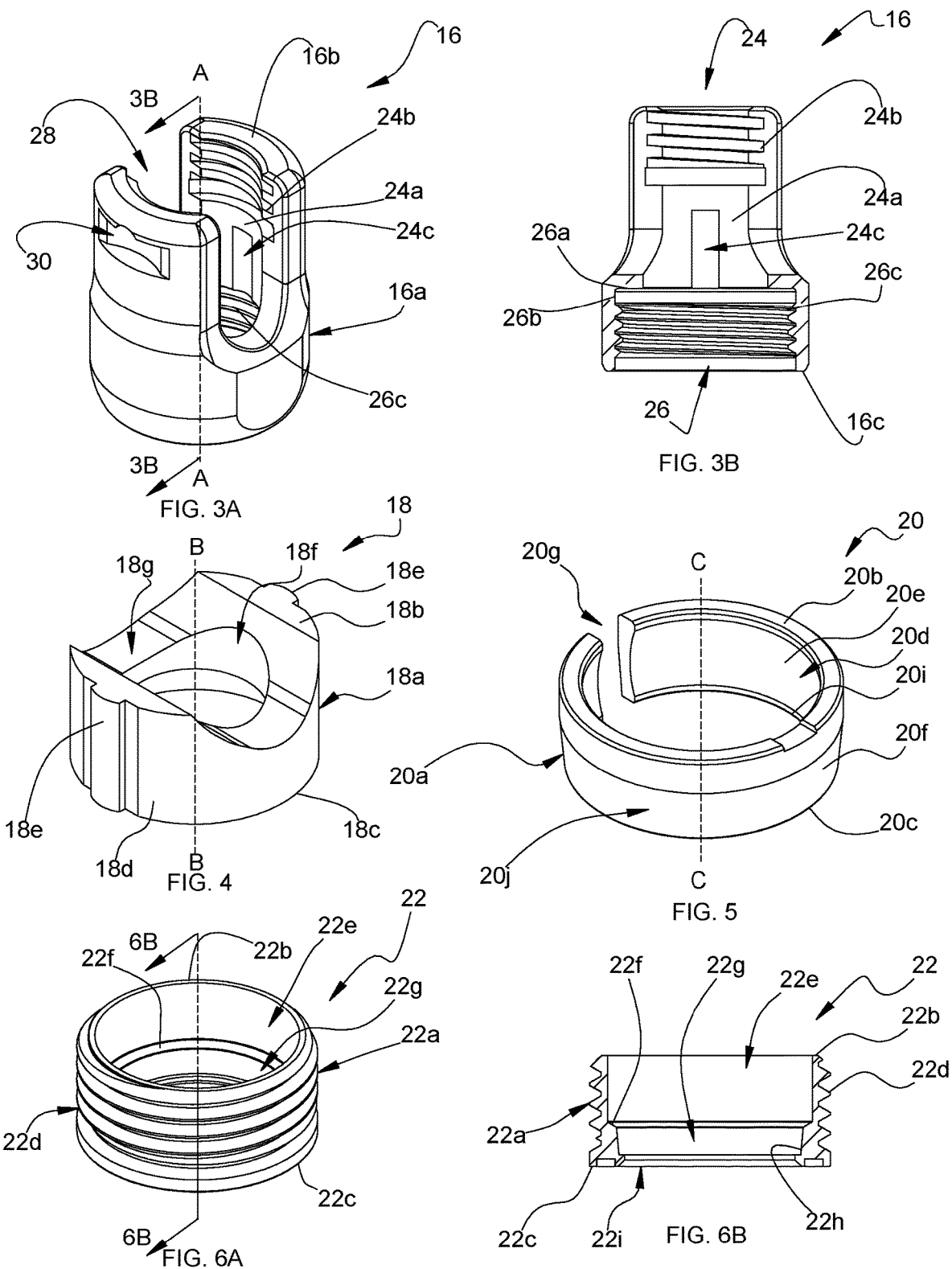

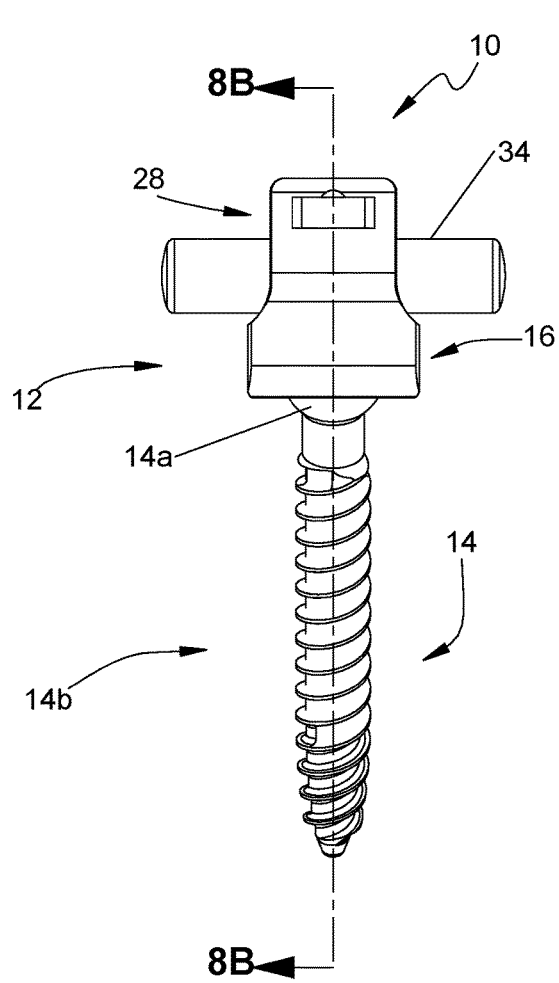
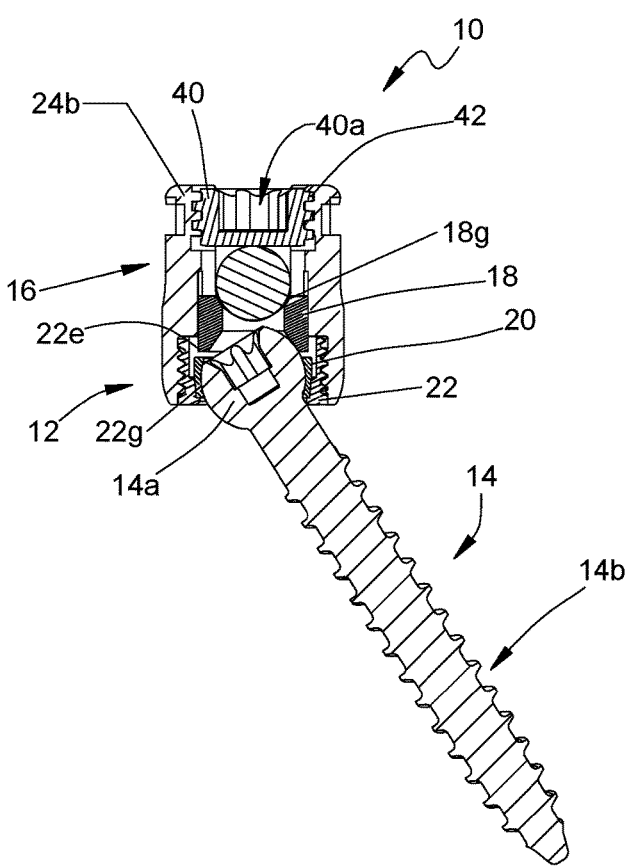
Fig. 8A
Fig. 8B

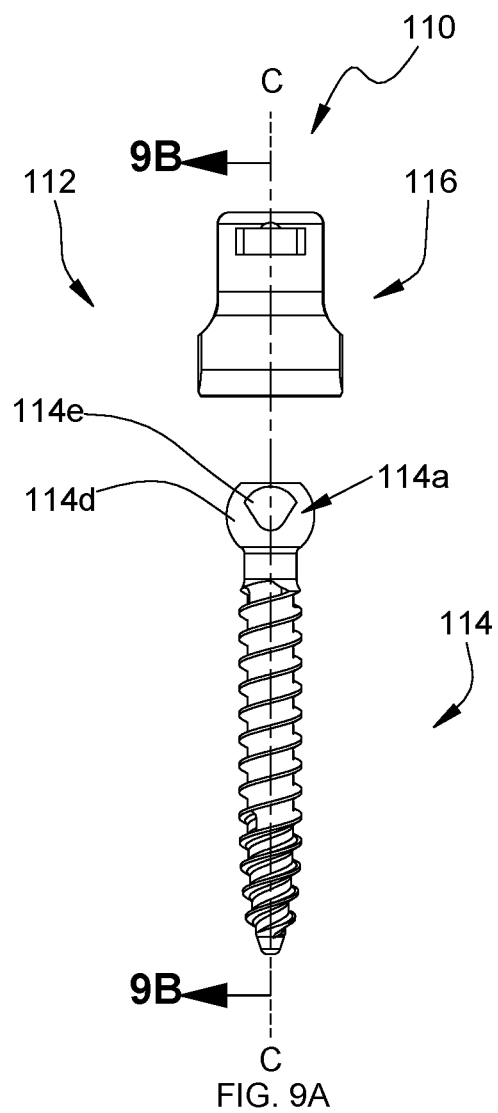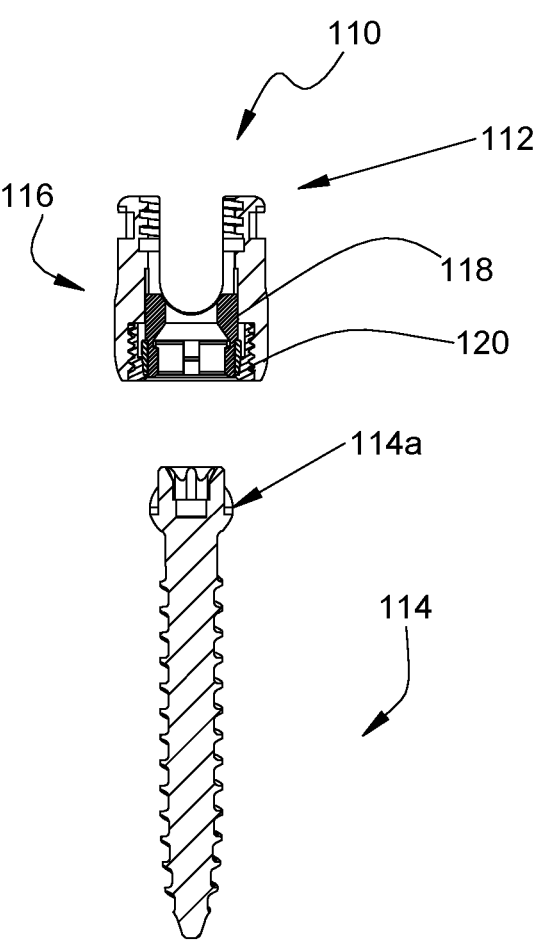
FIG. 9A
FIG. 9B

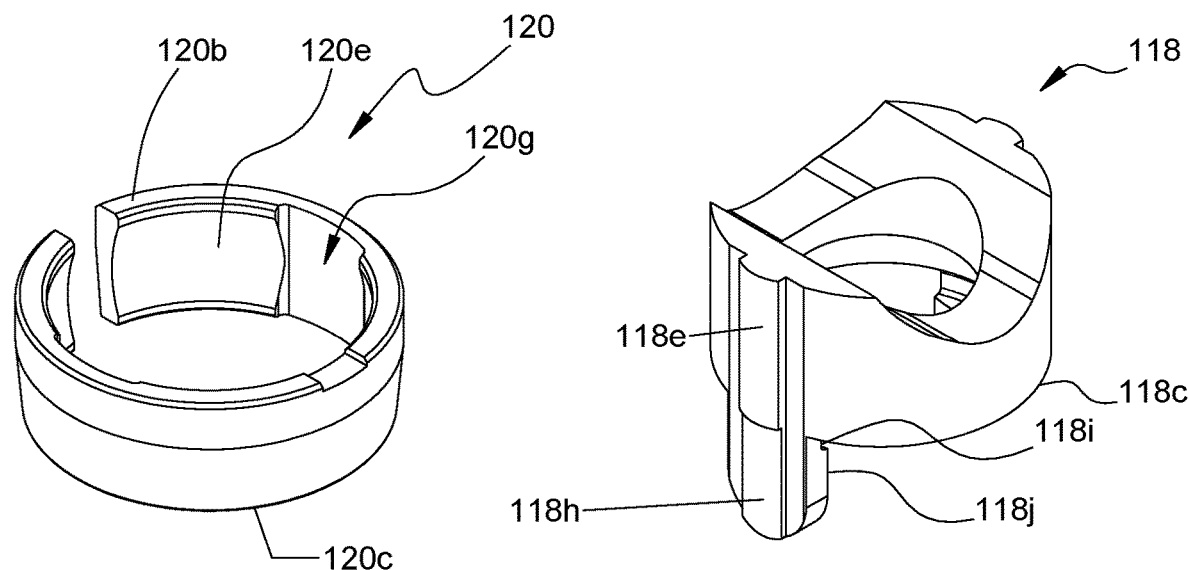
Fig. 11
Fig. 12
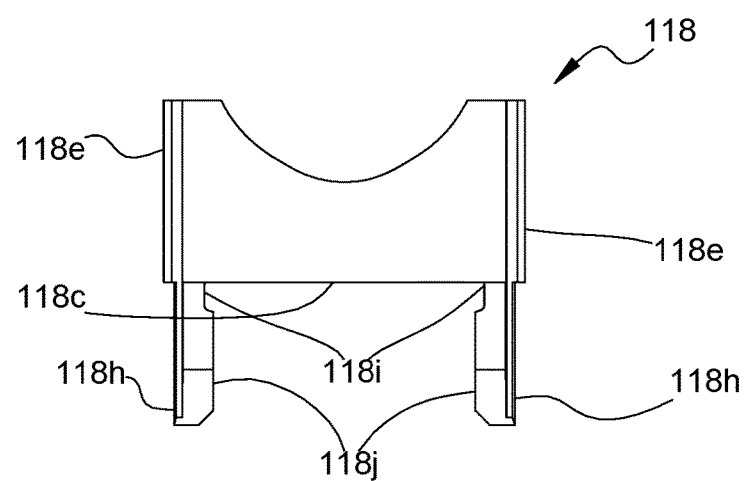
Fig. 13

MODULAR SPINAL FIXATION DEVICE

CROSS-REFERENCE TO RELATED APPLICATIONS

The present application is a national phase entry under 35 U.S.C. § 371 of International Application No. PCT/US2018/014179, filed Jan. 18, 2018, which claims priority to and the benefit of U.S. Provisional Patent Application No. 62/447,515, filed on Jan. 18, 2017, and U.S. Provisional Patent Application No. 62/487,516, filed on Apr. 20, 2017, the entire contents of each of which are hereby incorporated by reference herein.

BACKGROUND

Technical Field

The present disclosure relates to spinal fixation devices. More particularly, the present disclosure relates to head assemblies for use in modular spinal fixation devices that are connectable to spinal rods used in spinal constructs.

Description of Related Art

There are many known spinal conditions, e.g., scoliosis, that require the imposition and/or maintenance of corrective forces on the spine in order to return the spine to its normal condition. As a result, numerous devices (e.g., alignment systems) have been developed for use in spinal fixation. One type of spinal construct may include, for example, one or more spinal rods that can be placed parallel to the spine with fixation devices (such as hooks, screws, or plates) interconnected between the spinal rods and selected portions of the spine. The spinal rods can be connected to each other via cross-connecting members to provide a more rigid support and alignment system. In some cases, the use of these devices may be permanently implanted in the patient. In other cases, the devices may be implanted only as a temporary means of stabilizing or fixing the bones or bone fragments, with subsequent removal when no longer needed.

When using screws, the surgeon directs the screw into the vertebral body before attaching any additional mechanical hardware, such as rods or bands. In this manner, the surgeon typically attaches the spinal fixation devices to the spine in appropriate anatomical positions and then attaches the spinal rod to the fixation devices. In conjunction, the surgeon manipulates the spinal column and/or individual vertebra to provide the desired treatment for the spinal defect. Subsequently, the spinal rod and fixation devices are locked in a desired arrangement.

While the aforementioned spinal fixation devices are suitable for the above uses, there may exist a need for spinal fixation devices that can reduce the time and labor required by a user to insert a fixation device, such as a screw, into a vertebra.

SUMMARY

A spinal fixation device is provided in accordance with the present disclosure and includes modular head assembly and a bone screw. The modular head assembly includes a housing, an anvil, an insert, and a snap ring. The housing defines a proximal surface and an opposite, distal surface, the proximal and distal surfaces defining a throughbore therethrough. The anvil is configured to be slidably received within a portion of the throughbore. The insert defines a proximal surface and an opposite, distal surface. The distal surface defines a first counterbore therein terminating at a first annular surface. The first annular surface defines a second counterbore therein terminating at a second annular surface. The snap ring is configured to be disposed within the first counterbore of the insert when in a first configuration, and within the second counterbore of the insert when in a second configuration. The bone screw defines a head at a proximal portion thereof and a shank extending distally from the head. The bone screw is configured to be received within a portion of the snap ring.

In aspects, the distal surface of the housing may define a third counterbore therein terminating at an annular face.

In other aspects, the annular face of the third counterbore may define a slot extending in a proximal direction. The slot extending through an inner surface of the throughbore.

In certain aspects, the anvil may define a proximal surface and an opposite, distal surface, defining an outer surface extending therebetween. The outer surface defines a tab extending between the proximal and distal surfaces, the tab configured to be slidably received within the slot.

In other aspects, an inner surface of the third counterbore may define threads thereon.

In aspects, the insert may define an outer surface extending between the proximal and distal surfaces, the outer surface defining threads thereon configured to threadably engage the threads of the third counterbore.

In certain aspects, the snap ring may define a proximal surface and an opposite, distal surface, the proximal and distal surfaces defining a lumen therethrough.

In aspects, the proximal and distal surfaces of the snap ring may define an outer surface extending therebetween, the outer surface defining a slot extending through the proximal and distal surfaces and being in open communication with the lumen.

In other aspects, the lumen of the snap ring may define a longitudinal axis extending along a centerline thereof, the lumen defining an inner surface having a concave profile extending along the longitudinal axis.

In certain aspects, the snap ring may be formed from a resilient material.

In other aspects, an intersection of the outer surface of the snap ring and the distal surface of the snap ring may define an undercut configured to abut a portion of the second counterbore of the insert.

According to another aspect of the present disclosure, a method of assembling a spinal fixation device is provided and includes assembling a modular head assembly, including advancing an anvil within a throughbore defined through a proximal and distal surface of a housing, advancing a snap ring within a first counterbore defined through a proximal surface on an insert, and rotating the insert in a first direction to threadably engage a first plurality of threads defined on an outer surface of the insert with a second plurality of threads defined on an inner surface of a second counterbore defined through the distal surface of the housing until the insert is threadably coupled to the housing. The method further includes placing a bore defined through a distal surface of the insert adjacent a head of a bone screw and advancing the modular head assembly toward the head of the bone screw such that the head of the bone screw is received within the bore of the insert, and thereafter, within a lumen defined through distal and proximal surfaces of the snap ring to retain the head of the bone screw therein.

In certain aspects, advancing the anvil within the throughbore of the housing may include advancing a tab defined on an outer surface of the anvil within a slot defined within an inner surface of the throughbore to inhibit rotation of the anvil relative to the housing.

In other aspects, advancing the head of the bone screw within the lumen of the snap ring may include advancing the head of the bone screw within the lumen of the snap ring such that a concave profile defined on an inner surface of the lumen engages the head of the bone screw to retain the head of the bone screw within the lumen.

In aspects, advancing the head of the bone screw within the lumen of the snap ring may include the snap ring defining a slot extending through an outer surface thereof and extending through the proximal and distal surfaces, the slot enabling the snap ring to expand to a second, expanded state, as the head of the bone screw is received within the lumen, and return to a first, unexpanded state once the head of the bone screw is fully received within the lumen.

In certain aspects, the method may include advancing a spinal rod within a slot defined through an outer surface of the housing and extending through the proximal surface thereof.

In aspects, the method may include rotating a set screw in a first direction to threadably engage threads defined on an outer surface of the set screw with threads defined on an inner surface of the throughbore of the housing, wherein rotation of the set screw in the first direction causes the set screw to translate in a distal direction which causes a corresponding distal translation of the spinal rid, the anvil, and the snap ring.

In other aspects, the method may include further rotating the set screw in the first direction to cause the snap ring to further translate in a distal direction and be received within a second counterbore defined through a first annular surface defined by the first counterbore of the insert, wherein reception of the snap ring within the second counterbore causes the snap ring to compress around the head of the bone screw and lock the orientation of the bone screw relative to the modular head assembly.

In accordance with another aspect of the present disclosure, a method of assembling a spinal fixation device is provided and includes advancing a bone screw within an incision formed in a patient's body, driving the bone screw into a vertebra, the bone screw including a head at a proximal portion thereof and a threaded shank extending distally from the head. The method further includes assembling a modular head assembly, including advancing an anvil within a throughbore defined through a proximal and distal surface of a housing, advancing a snap ring within a first counterbore defined through a proximal surface of an insert, and rotating the insert in a first direction to threadably engage a first plurality of threads defined on an outer surface of the insert with a second plurality of threads defined on an inner surface of a second counterbore defined through the distal surface of the housing until the insert is threadably coupled to the housing. The method further includes placing a bore defined through a distal surface of the insert adjacent the head of the bone screw and advancing the modular head assembly toward the head of the bone screw such that the head of the bone screw is received within the bore of the insert, and thereafter, within a lumen defined through distal and proximal surfaces of the snap ring to retain the head of the bone screw therein.

BRIEF DESCRIPTION OF THE DRAWINGS

Various embodiments of the present disclosure are described hereinbelow with references to the drawings, wherein:

FIG. 3A is a perspective view of a housing of the modular head assembly of FIG. 1A;

FIG. 3B is a cross-sectional view of the housing of FIG. 3A, taken along section-line 3B-3B of FIG. 3A;

FIG. 4 is a perspective view of an anvil of the modular head assembly of FIG. 1A;

FIG. 5 is a perspective view of a snap-ring of the modular head assembly of FIG. 1A;

FIG. 6A is a perspective view of an insert of the modular head assembly of FIG. 1A;

FIG. 6B is a cross-sectional view of the insert of FIG. 6A, taken along section-line 6B-6B of FIG. 6A;

FIG. 8A is a front view of the spinal fixation device of FIG. 1A, shown with a spinal rod and set screw in accordance with the present disclosure;

FIG. 8B is a section view of the spinal fixation device of FIG. 1A and the spinal rod and set screw of FIG. 8A, taken along section-line 8B-8B of FIG. 8A;

FIG. 9A is a front view of another embodiment of a spinal fixation device including a modular head assembly and bone screw provided in accordance with the present disclosure;

FIG. 9B is a cross-sectional view of the spinal fixation device of FIG. 9A, taken along section-line 9B-9B of FIG. 9A;

FIG. 11 is a perspective view of a snap ring of the modular head assembly of FIG. 9A;

FIG. 12 is a perspective view of an anvil of the modular head assembly of FIG. 9A;

FIG. 13 is a front view of the anvil of FIG. 12;

DETAILED DESCRIPTION

Figures 1A, 1B:
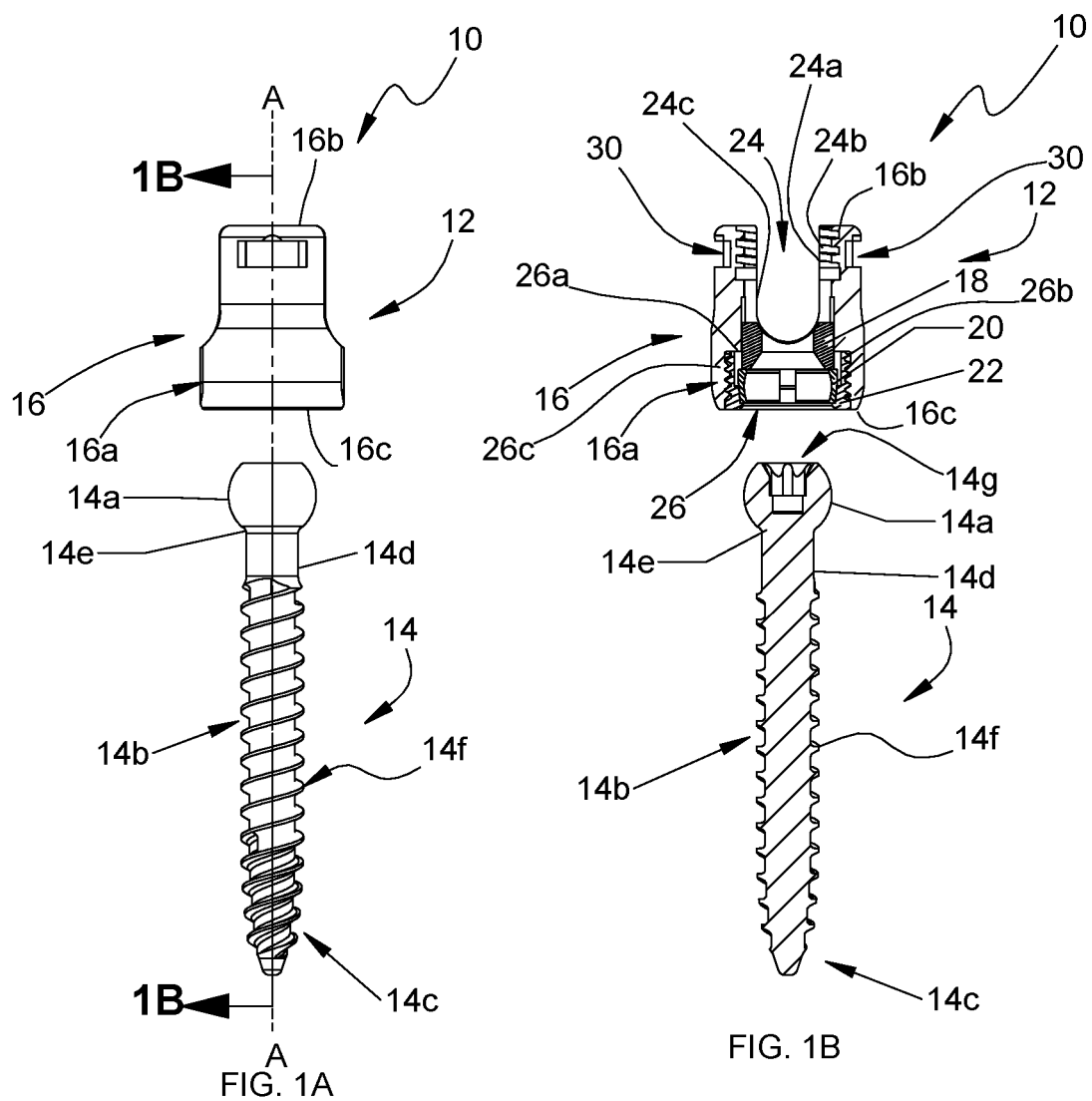
FIG. 1A is a front view of a spinal fixation device including a modular head assembly and a bone screw in accordance with an embodiment of the present disclosure.
FIG. 1B is a cross-sectional view of the spinal fixation device of FIG. 1A, taken along section-line 1B-1B of FIG. 1A.

Embodiments of the present disclosure are now described in detail with reference to the drawings in which like reference numerals designate identical or corresponding elements in each of the several views. As used herein, the term "clinician" refers to a doctor, a nurse or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

Figure 2:
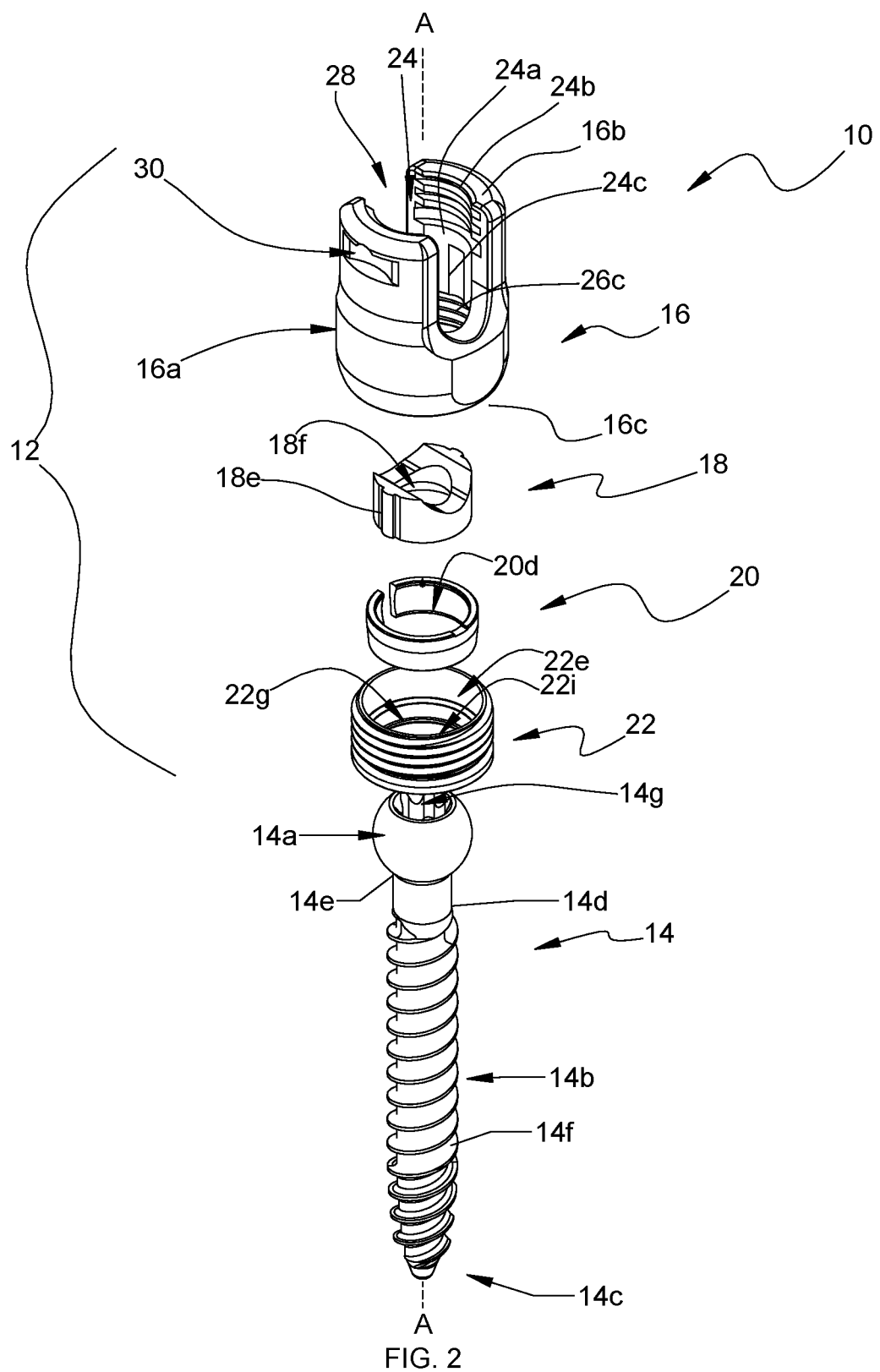
FIG. 2 is a perspective view of the spinal fixation device of FIG. 1A, shown with parts separated.

Referring now to the drawings, FIGS. 1A, 1B, and 2 illustrate an embodiment of a spinal fixation device provided in accordance with the present disclosure and generally identified as reference numeral 10. The spinal fixation device 10 includes a modular head assembly 12 and a bone screw 14, although it is contemplated that the spinal fixation device may only include the modular head assembly 12, depending upon the needs of the procedure being performed. As can be appreciated, it is contemplated that the modular head assembly 12 may be utilized with a spinal hook or other similar spinal fixation devices.

The modular head assembly 12 includes a housing 16, an anvil 18, a snap ring 20, and an insert 22. With additional reference to FIGS. 3A and 3B, the housing 16 includes a body portion 16a extending between a proximal surface 16b and an opposite, distal surface 16c defining a longitudinal axis A-A therethrough. Although generally illustrated as having a cylindrical profile, it is contemplated that the body portion 16a may include any suitable profile capable of being used during spinal surgery. The proximal surface 16b of the housing 16 defines a through-hole 24 therethrough that extends through the distal surface 16c of the housing 16. An inner surface 24a of a proximal portion of the through-hole 24 defines a plurality of threads 24b configured to threadably engage a set screw 40 (FIG. 8B), as will be described in further detail hereinbelow. A distal portion of the inner surface 24a of the through-hole 24 defines a pair of slots 24c disposed in juxtaposed relation to one another and extending along the longitudinal axis A-A. Although illustrated as defining a pair of slots 24c, it is contemplated that the inner surface 24a of the through-hole 24 may define only one slot 24c. Each slot 24c is configured to slidably engage a corresponding feature of the anvil 18 to enable translation of the anvil 18 within the through-hole 24, but inhibit rotation of the anvil 18 within the through-hole 24. In this manner, the pair of slots 24c ensures that a U-shaped slot 28 of the housing 16 remains aligned with a concave relief 18g (FIG. 4) defined in the anvil 18, as will be described in further detail hereinbelow.

The distal surface 16c of the body portion 16a defines a counterbore 26 extending towards the proximal surface 16b and terminating at an annular face 26a located at a middle portion of the body portion 16a, although it is contemplated that the counterbore 26 may extend any suitable distance from the lower portion 16c. An inner surface 26b of the counterbore 26 defines a plurality of threads 26c configured to threadably engage the insert 22, as will be described in further detail hereinbelow.

An outer surface 16d of the body portion 16a of the housing 16 defines a U-shaped slot 28 therethrough and extending through the proximal surface 16b thereof. As can be appreciated, the U-shaped slot 28 is configured to receive a spinal rod 34 (FIG. 8A), as will be described in further detail hereinbelow. As illustrated in FIG. 2, the outer surface 16d of the body portion 16a defines a pair of reliefs 30 therein which are aligned with the U-shaped slot 28 (e.g., oriented transverse to the longitudinal axis A-A). The pair of reliefs 30 is configured to engage a suitable tool (not shown) to enable a clinician to grasp and manipulate the modular head assembly 12 during the surgical procedure. It is contemplated that the housing 16 may be formed from any biocompatible material suitable for use in surgical procedures, such as metallic materials (e.g., titanium (e.g., commercially pure titanium), titanium alloys, (e.g., Ti-6Al-4V), stainless steels, cobalt chrome alloys, etc.) or non-metallic materials (e.g., ceramics, polyetheretherketone (PEEK), etc.).

With additional reference to FIG. 4, the anvil 18 defines a body portion 18a extending between a proximal surface 18b and an opposite, distal surface 18c defining a longitudinal axis B-B therethrough. The body portion 18a includes a profile that is complimentary to the profile of the through-hole 24 of the housing 16 such that the anvil 18 is capable of being slidably received therein. An outer surface 18d of the body portion 18a defines a pair of tabs 18e thereon extending along the longitudinal axis B-B. In embodiments, it is contemplated that the outer surface 18d may form only a single tab 18e thereon. Each tab 18e is oriented 180 degrees apart relative to the other tab 18e such that each tab 18e of the pair of tabs 18e is received within a corresponding slot 24c of the pair of slots 24c of the housing 16 to permit the anvil 18 to translate within the through-hole 24 along axis A-A, but inhibit rotation of the anvil 18 relative thereto. The proximal and distal surfaces 18b, 18c define a bore 18f therethrough. The proximal surface 18b defines a relief 18g therein having a concave profile (e.g., extending toward the distal surface 18c) and configured to receive a portion of the spinal rod 34 (FIG. 8A) therein. As can be appreciated, the anvil 18 may be formed from any material suitable for use in surgical procedures, such as those described hereinabove, and may be formed from the same or a different material than the housing 16.

The snap ring 20 is illustrated in FIG. 5 and is configured to be slidably received within a portion of the insert 22 (FIG. 1B), as will be described in further detail hereinbelow. The snap ring 20 includes a generally cylindrical body 20a extending between an upper surface 20b and an opposite, lower surface 20c defining a longitudinal axis C-C therethrough. Although generally illustrated as having a cylindrical profile, it is contemplated that the body 20a may include any suitable profile, and may conform to the profile of the portion of the insert 22 in which the snap ring 20 is configured to be received. The upper and lower surfaces 20b, 20c define a lumen 20d therethrough which defines a curvate inner surface 20e thereon. The curvate inner surface 20e defines a generally concave profile extending along the longitudinal axis C-C and generally corresponds to the profile of a head 14a of the bone screw 14 (FIG. 2). An outer surface 20f of the body 20a defines a slot 20g therethrough extending through the inner surface 20e of the lumen 20d and through the upper and lower surfaces 20b, 20c such that the slot 20g is in open communication with the lumen 20d. In this manner, the slot 20g interrupts a perimeter of the snap ring 20 such that the snap ring 20 forms a generally C-shaped profile which enables the body 20a to expand and compress (e.g., the outer diameter of the body 20a increases or decreases) due to an external or internal force being applied thereto. The proximal surface 20b defines a channel 20g therein extending transverse to the longitudinal axis C-C and disposed opposite to the slot 20d. The intersection of the distal surface 20b and the inner surface 20f of the body 20a defines a bevel 20i that extends towards the lumen 20d. The intersection of the distal surface 20c and the outer surface 20f of the body 20a defines an undercut 20j that extends towards the lumen 20d. It is contemplated that the snap ring 20 may be formed from any material suitable for use in surgical procedures such as those described hereinabove, and may be formed from the same or a different material than the housing 16 and the anvil 18. In one non-limiting embodiment, the snap ring 20 is formed from a resilient material that enables the snap ring to expand and compress without being permanently deformed.

Turning now to FIGS. 6A and 6B, an embodiment of the insert 22 is illustrated. The insert 22 includes a body 22a defining a generally cylindrical profile extending between a proximal surface 22b and an opposite, distal surface 22c. An outer surface of the body 22a defines a plurality of threads 22d configured to threadably engage the plurality of threads 26c of the counterbore 26 of the housing 16 such that the insert 22 may be threadably coupled to the housing 16. The proximal surface 22b defines a first counterbore 22e therein terminating at a first annular surface or annular shoulder 22f disposed approximately halfway between the proximal and distal surfaces 22b, 22c of the body 22a. In embodiments, it is contemplated that the first annular surface 22f may be disposed at any suitable location depending upon the needs of the procedure being performed. The first annular surface 22f defines a second counterbore 22g therein terminating at a second annular surface or annular shoulder 22h disposed adjacent the distal surface 22c of the body 22a. The second counterbore 22g is concentric with the first counterbore 22e and includes a diameter that is less than the first counterbore 22e. In this manner, the first counterbore 22e is configured to slidably receive the snap ring 20 therein whereas the second counterbore 22g is configured to compress the snap ring 20 as the snap ring 20 is received therein. In this manner, the second counterbore 22g compresses around a head of the bone screw 14 to secure the bone screw 14 in position relative to the housing 16, as will be described in further detail hereinbelow.

The second annular surface 22h of the second counterbore 22g defines a bore 22i therethrough and extending through the distal surface 22c of the body 22a. Although generally illustrated as being disposed concentric with the second counterbore 22g, it is contemplated that the bore 22i may be defined at any suitable location on the second annular surface 22h. The bore 22i defines a diameter capable of permitting the head of the bone screw 14 to pass therethrough, as will be described in further detail below. It is contemplated that the insert 22 may be formed from any material suitable for use in surgical procedures such as those described hereinabove, and may be formed from the same or a different material than the housing 16, anvil 18, and/or snap ring 20. In embodiments, the insert 22 is formed from a material that is as hard or harder than the material forming the snap ring 20, such that neither the snap ring 20 nor the insert 22 is damaged as the snap ring 22 transitions from the first counterbore 22e to the second counterbore 22g of the insert 22.

Returning to FIGS. 1A, 1B, and 2, an embodiment of a bone screw 14 capable of being used with the modular head assembly 12 is illustrated. Although generally illustrated as being a poly-axial pedicle screw, it is contemplated that the bone screw 14 may be any suitable bone screw capable of being used during spinal surgery (e.g. mono-axial or uniaxial). The bone screw 14 includes a head 14a at a proximal end thereof and a shank 14b extending distally therefrom. The shank 14b includes a distal tip portion 14c, an elongated body portion 14d, and a proximal end 14e that is coupled to the head 14a (e.g., monolithically formed therewith). The distal tip portion 14c is generally conically-shaped to facilitate insertion of the bone screw 14 into bone, and in embodiments, may be self-tapping or self-starting. The elongated body portion 14d of the shank 14b includes a substantially uniform outer diameter and includes a continuous helical thread 14f of substantially uniform pitch formed thereon to allow for threaded insertion and retention of the bone screw 14 within the bone. It is contemplated that the thread 14f disposed about the elongated body portion 14d of the shank 14b may be single threaded, double threaded, etc., depending upon the needs of the procedure being performed. In embodiments, it is contemplated that the shank 14b may be cannulated to permit passage of a guide wire (not shown) or other instrumentation therethrough.

Figure 18A:
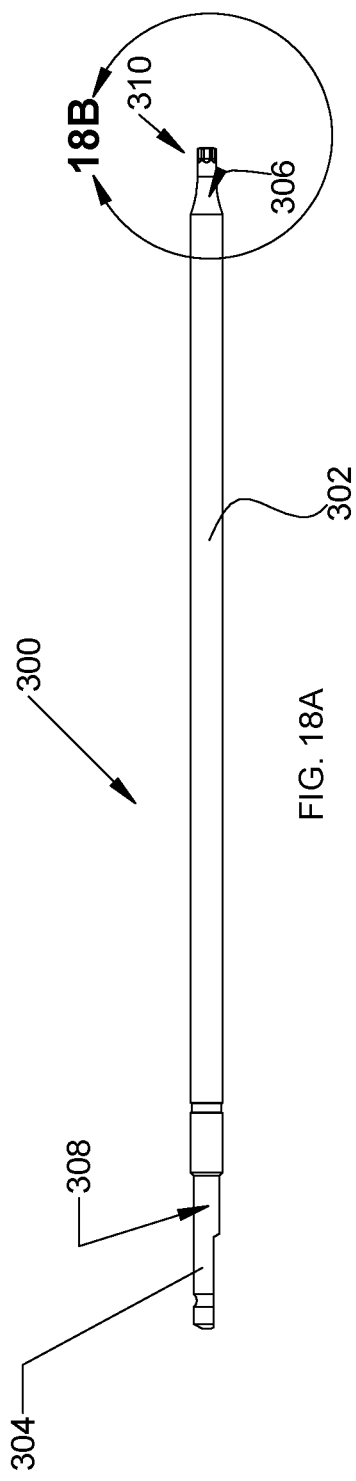
FIG. 18A is a side view of an insertion tool.
Figure 18B:
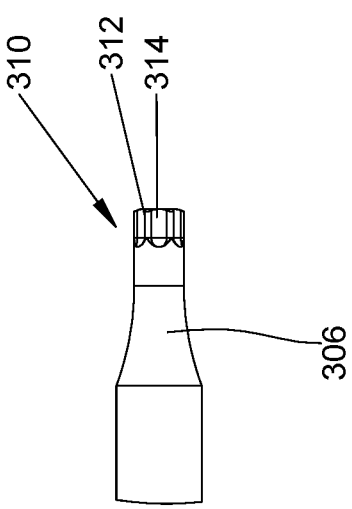
FIG. 18B is a detail view of the area of detail indicated in FIG. 18A.

The head 14a of the bone screw 14 defines a generally spherical shape and defines a tool engaging recess 14g at a proximal portion thereof that is configured to engage the engagement region 310 of the driver 300 (FIGS. 18A, 18B). As can be appreciated, the tool engaging recess 14g may define any suitable shape capable of transmitting the rotational motion of the tool to the head 14a of the bone screw, and in one non-limiting embodiment, may define a hexalobe configuration. It is contemplated that the bone screw 14 may be formed from any material suitable for use in surgical procedures such as those described hereinabove, and may be formed from the same or a different material than the housing 16, the anvil 18, the snap ring 20, and/or the insert 22. In embodiments, the head 14a of the bone screw 14 may be formed from a different material than the shank 14b of the bone screw.

For a detailed description of the construction of a bone screw capable of being utilized with the modular head assembly 10 described herein, reference may be made to U.S. Pat. No. 9,393,048, titled "Polyaxial Bonescrew Assembly," the entire contents of which is hereby incorporated by reference herein.

Figures 7A, 7B:
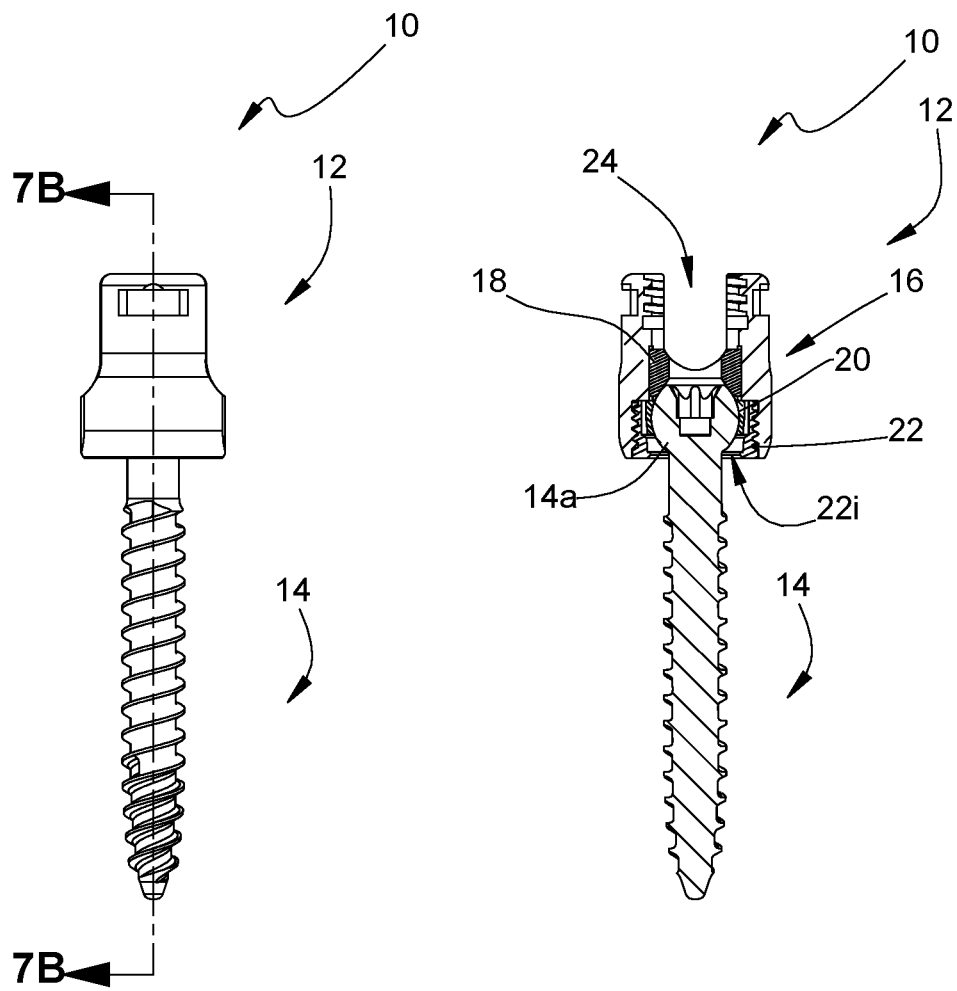
FIG. 7A is a front view of the spinal fixation device of FIG. 1A, shown in an assembled state.
FIG. 7B is a cross-sectional view of the spinal fixation device of FIG. 1A, taken along section-line 7B-7B of FIG. 7A.

With reference to FIGS. 2, 7A, and 7B, a method of assembling the spinal fixation device 10 is illustrated. Initially, the anvil 18 is positioned below the counterbore 26 of the housing 16 with the pair of tabs 18e of the anvil aligned with the pair of slots 24c of the housing 16. The anvil 18 is urged in a proximal direction into the counterbore 26 such that the pair of tabs 18e is received within the pair of slots 24c.

FIGS. 7A and 7B illustrate the spinal fixation system 10 in an assembled state. Initially, the modular head assembly 12 of the spinal fixation system 10 is assembled by first aligning the pair of tabs 18e of the anvil with the corresponding pair of slots 24c of the through-hole 24 of the housing 16. Once the pair of tabs 18e is in alignment with the pair of slots 24c, the anvil is advanced in a proximal direction within the through-hole 24 until an upper portion of the pair of tabs 18e abuts a proximal-most portion of the pair of slots 24c. Next, the snap ring 20 is placed adjacent the counterbore 26 of the housing 16 and advanced in a proximal direction such that the snap ring 20 is slidably received therein. With the snap ring 20 received within the counterbore 26, the insert 22 is initially placed adjacent the counterbore 26 of the housing 16. The insert 22 is then rotated in a first direction such that the plurality of threads 22d of the insert threadably engages the corresponding plurality of threads 26c of the counterbore 26 of the housing 16. The insert 22 is further rotated until the insert 22 is fully received within the counterbore 26. In this position, the anvil 18 is in a proximal most position and the snap ring 20 is disposed within the first counterbore 22e of the insert 22 such that the snap ring 20 is in a first, uncompressed state.

With the modular head assembly 12 in an assembled state, the bone screw 14 is driven into bone using the driver 300 (FIGS. 18A, 18B) engaged with the tool engaging recess 14g of the head 14a of the bone screw 14. With the bone screw 14 secured at a desired location, the modular head assembly 12 is placed adjacent the head 14a of the bone screw 14. The modular head assembly 12 is then advanced in a distal direction such that the head 14a of the bone screw 14 is received within the bore 22i of the insert 22, and thereafter, within the lumen 20d of the snap ring 20. As the head 14a of the bone screw 14 advances within the bore 22i of the snap ring 20, the head 14a causes the snap ring 20 to expand (e.g., the diameter enlarges) to accept the head 14a therein. As can be appreciated, the concave inner surface 20e of the lumen 20d conforms to the spheroid profile of the head 14a such that the diameter of the snap ring 20 reduces from an expanded state during insertion of the head 14a therein to a compressed state where the inner diameter of the lumen 20d conforms to the diameter of the head 14a and provides a compressive force thereon (e.g., an intermediate position that is between the expanded state and the clamped state described hereinbelow).

With additional reference to FIGS. 8A and 8B, it is contemplated that the axial orientation of the bone screw 14 relative to the modular head assembly 10 may be locked when a suitable spinal rod 34 is secured within the housing 16 using a suitable set screw 40. In this manner, the spinal rod 34 is inserted within the U-shaped slot 28 of the housing 16 and is received within the relief 18g and abuts the anvil 18. At this point, using a suitable tool or driver 300 (FIGS. 18A and 18B) inserted within a tool engaging recess 40a defined within the set screw 40, the set screw 40 is inserted into the through-hole 24 of the housing. The set screw 40 defines a plurality of threads 42 thereon to threadably engage the plurality of threads 24b of the through-hole 24. In this manner, using the driver 300, the set screw 40 is rotated in a first direction to cause the set screw 40 to translate in a distal direction and urge the spinal rod 34 in a corresponding distal direction. Continued rotation of the set screw 40 in the first direction causes the set screw 40 to further urge the spinal rod 34 in a distal direction within the through-hole 24 and in turn, causes the spinal rod 34 to urge the anvil 18 in a distal direction. The distal translation of the anvil 18 urges the snap ring 20, along with the bone screw 14 captured therewithin, to translate into the second counterbore 22g of the insert 22. The smaller diameter of the second counterbore 22g causes the snap ring 20 to compress around the head 14a of the bone screw 14, thereby clamping the head 14a of the bone screw 14 and fixing the rotational and angular position of the bone screw 14 with respect the housing 16.

If the angle at which the modular head assembly 10 has been locked relative to the bone screw 14 is undesirable, or if the modular head assembly 10 must be removed for any reason, using the driver 300, the set screw 40 is rotated in a second, opposite direction to translate the set screw 40 in a proximal direction. Continued rotation of the set screw 40 in the second direction enables the set screw 40 to be removed from the through-hole 24 of the housing 16. As can be appreciated, it may not be necessary to completely remove the set screw 40 from the housing 16 to enable repositioning of the modular head assembly 10 relative to the bone screw 14. At this point, the housing 16 of the modular head assembly 10 may be urged in a distal direction. As the housing 16 translates relative to the bone screw 14, the head 14a of the bone screw 14 urges the snap ring 20 in a proximal direction, which in turn, causes the snap ring 20 to translate from the second counterbore 22g of the insert 22 to the first counterbore 22e of the insert 22. Translation from the second counterbore 22g to the first counterbore 22e enables the snap ring 20 to transition from a second, compressed state where the modular head assembly 10 is inhibited from movement relative to the bone screw 14, to the first, uncompressed state where the modular head assembly 10 is permitted to move relative to the bone screw 14. At this point, the modular head assembly 10 may be placed in the desired position relative to the bone screw 14 and modular head assembly 10 may be locked relative to the bone screw using the procedure described hereinabove.

Figure 10:
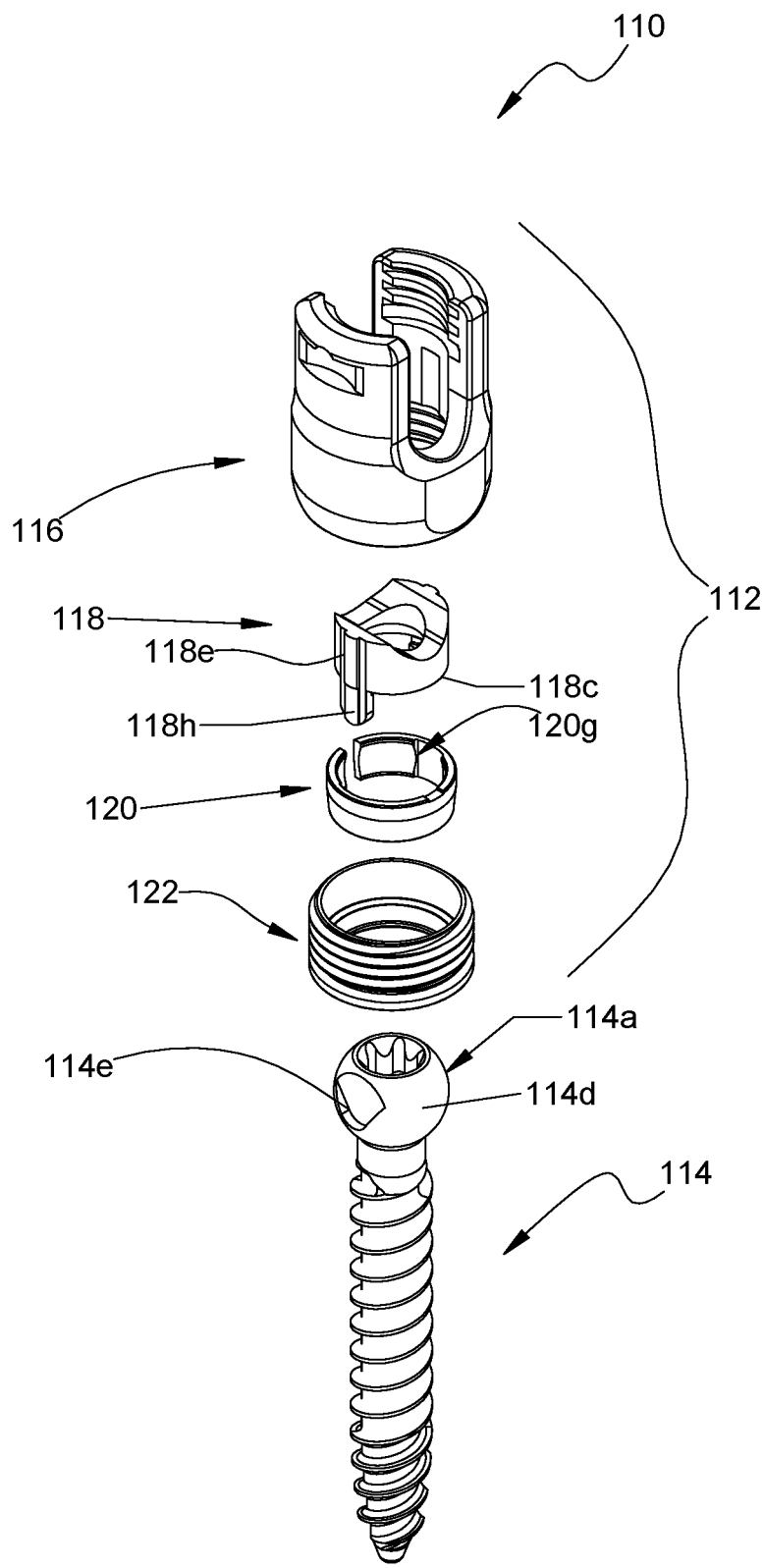
FIG. 10 is a perspective view of the spinal fixation device of FIG. 9A, shown with parts separated.

Turning to FIGS. 9A, 9B, and 10, another embodiment of a spinal fixation device is illustrated and generally identified by reference numeral 110. The spinal fixation device 110 is substantially similar to the spinal fixation device 10, and therefore, only the differences therebetween will be described hereinbelow in the interest of brevity.

With reference to FIGS. 10 and 12, the pair of tabs 118e of the anvil 118 extend distal of the lower surface 118c to define a corresponding pair of extensions 118h. In embodiments, only a single extension 118h may be defined regardless of if there is only a single tab 118e or a pair of tabs 118e defined on the anvil 118. An inner surface 118i of each extension of the pair of extensions 118h defines a barb or protrusion 118j extending toward one another (e.g., in an interior direction) and are configured to grasp a corresponding feature defined in the head 114a of the bone screw 114, as will be described in further detail hereinbelow.

With additional reference to FIG. 11, the inner surface 120e of the snap ring 120 defines a pair of opposed channels 120g therein extending through each of the upper and lower surfaces 120b, 120c. The pair of opposed channels 120g is configured to slidably receive the pair of extensions 118h of the anvil 118 and inhibit rotation of the snap ring 120 relative to the anvil 118, and in turn, the housing 116.

Returning to FIGS. 9A, 9B, and 10, another embodiment of a bone screw is provided and generally identified by reference numeral 114. The bone screw 114 is substantially similar to the bone screw 14 and therefore only the differences therebetween will be described hereinbelow in the interest of brevity. An outer surface 114d of the head 114 of bone screw 114 defines a pair of opposed reliefs 114e. The pair of reliefs 114e is disposed approximately at the equator (e.g., the widest portion of the head 114) and define a generally triangular profile such that the apex of the pair of reliefs is disposed adjacent the distal end of the head 114a. Each relief of the pair of reliefs 114e is configured to slidably receive a respective extension of the pair of extensions 118h of the anvil 118. The depth and width of the pair of reliefs 114d may vary depending upon how much angular movement of the bone screw 114 relative to the housing 116 is desired. In this manner, a pair of reliefs 114d having a smaller width will allow a corresponding small amount of angular movement of the bone screw 114 relative to the housing 116 of the modular head assembly 112. Similarly, a pair of reliefs 114e having a larger width will allow a corresponding larger amount of angular movement of the bone screw 114 relative to the housing 116. Further, the pair of reliefs 114e inhibits rotation of the bone screw 114 about the longitudinal axis C-C since after assembly, the pair of extensions 118h compress against the pair of reliefs 114e to constrain movement of the bone screw 114 to a single plane.

Figures 14A, 14B:
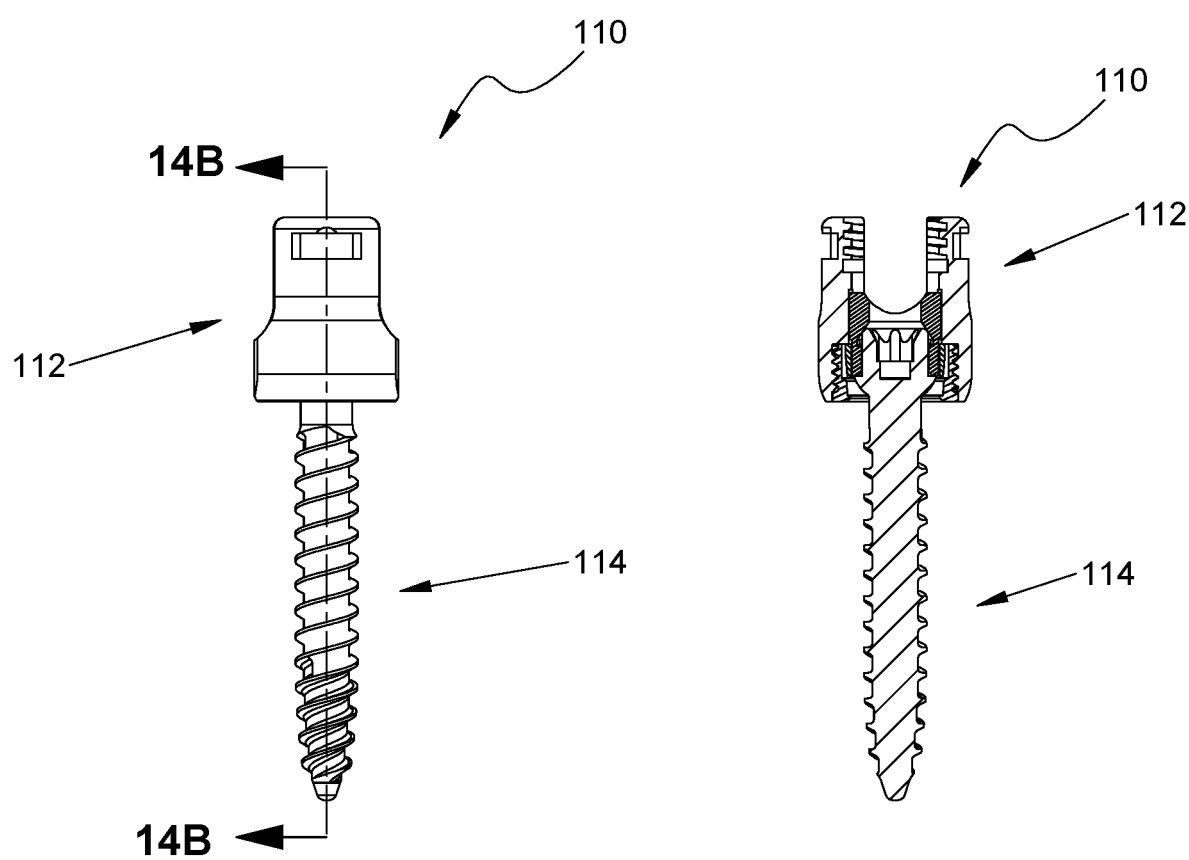
FIG. 14A is a front view of the spinal fixation device of FIG. 9A, shown in an assembled state.
FIG. 14B is a cross-sectional view of the spinal fixation device of FIG. 9A, taken along section-line 14B-14B of FIG. 14A.
Figures 15A, 15B:
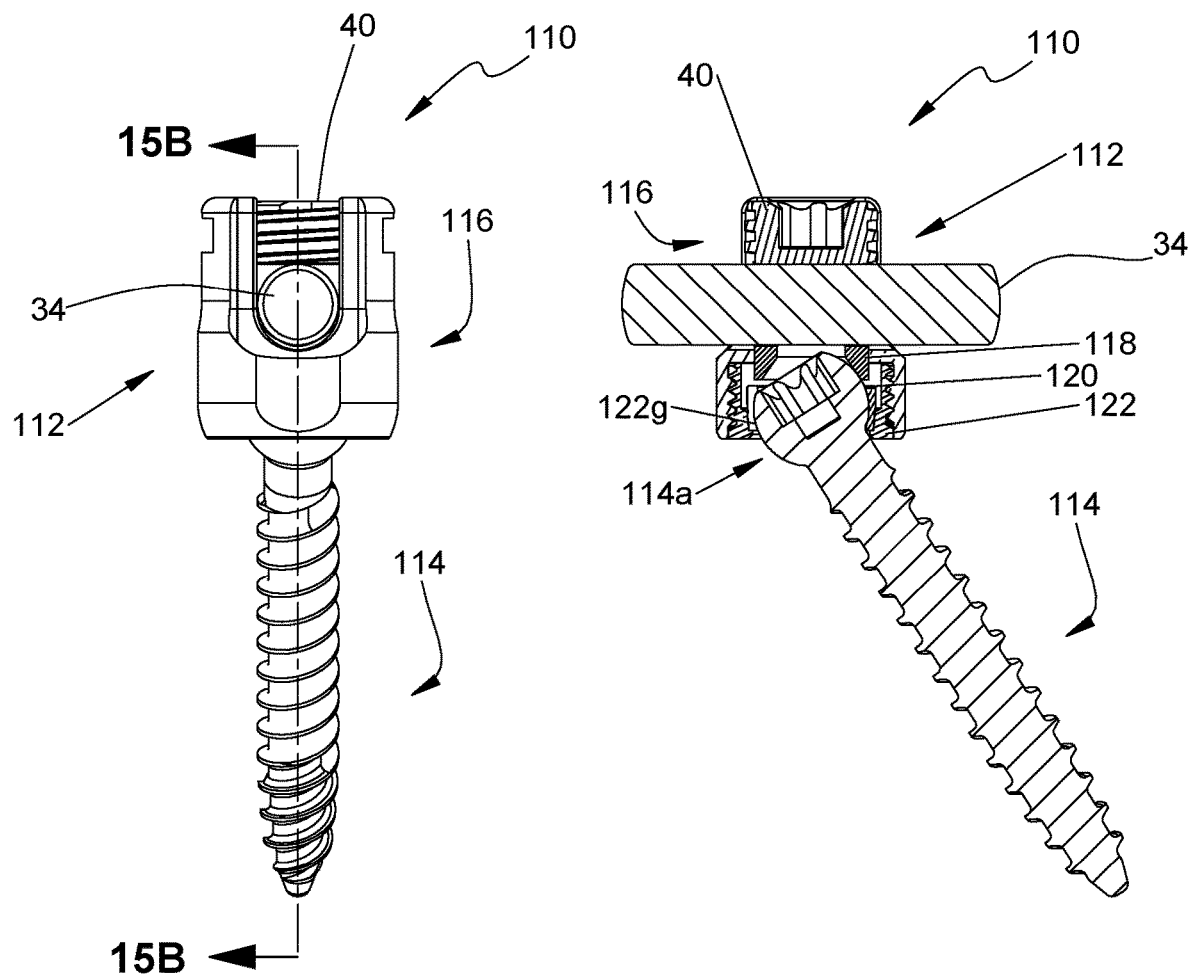
FIG. 15A is a side view of the spinal fixation device of FIG. 9A, shown with a spinal rod and set screw provided in accordance with the present disclosure.
FIG. 15B is a cross-sectional view of the spinal fixation device of FIG. 9A and the spinal rod and set screw of FIG. 15A, taken along section-line 15B-15B of FIG. 15A.

Assembly of the spinal fixation device 110 is substantially similar to the assembly of the spinal fixation device 10, and therefore only the differences therebetween will be described in detail hereinbelow. With additional reference to FIGS. 14A and 14B, during insertion of the snap ring 120 within the housing 116, the pair of opposed channels 120g of the snap ring is aligned with the pair of extensions 118h of the anvil 118 such that as the snap ring 120 is urged in a proximal direction, the pair of extensions 118h of the anvil 118 are received within the pair of opposed channels 120g. Similarly, the pair of reliefs 114e of the bone screw 114 is initially aligned with the pair of extensions 118h of the anvil 118. Thereafter, the bone screw 114 is urged in a proximal direction such that each extension of the pair of extensions 118h is received within a corresponding relief of the pair of reliefs 114e.

With reference to FIGS. 14A-15B, the process to lock the axial orientation of the bone screw 114 relative to the modular head assembly 112 is substantially similar to that of locking the bone screw 14 relative to the modular head assembly 12. Therefore, only the differences therebetween will be described herein in the interest of brevity. As the set screw 40 is rotated in the first direction to urge the spinal rod 34 in a distal direction, the anvil 118, along with the snap ring 120 is urged also urged in a distal direction and into the second counterbore 122g of the insert 122. The smaller diameter of the second counterbore 122g causes the snap ring 120 to compress around the head 114a of the bone screw 114, as well as the pair of extensions 118h of the anvil 118. In this manner, in addition to the compressive force applied to the head 114a of the bone screw 114, the snap ring 120 compresses the pair of extensions 118h against the pair of reliefs 114d to apply additional compressive force to the head 114a of the bone screw 114 to ensure the axial orientation of the bone screw 114 relative to the modular head assembly 112 is locked. The process to readjust the axial orientation of the bone screw 114 relative to the modular head assembly 112 is substantially similar to the process to readjust the axial orientation of the bone screw 14 relative to the modular head assembly 12 and therefore, will not be described herein in detail.

Figures 16A, 16B:
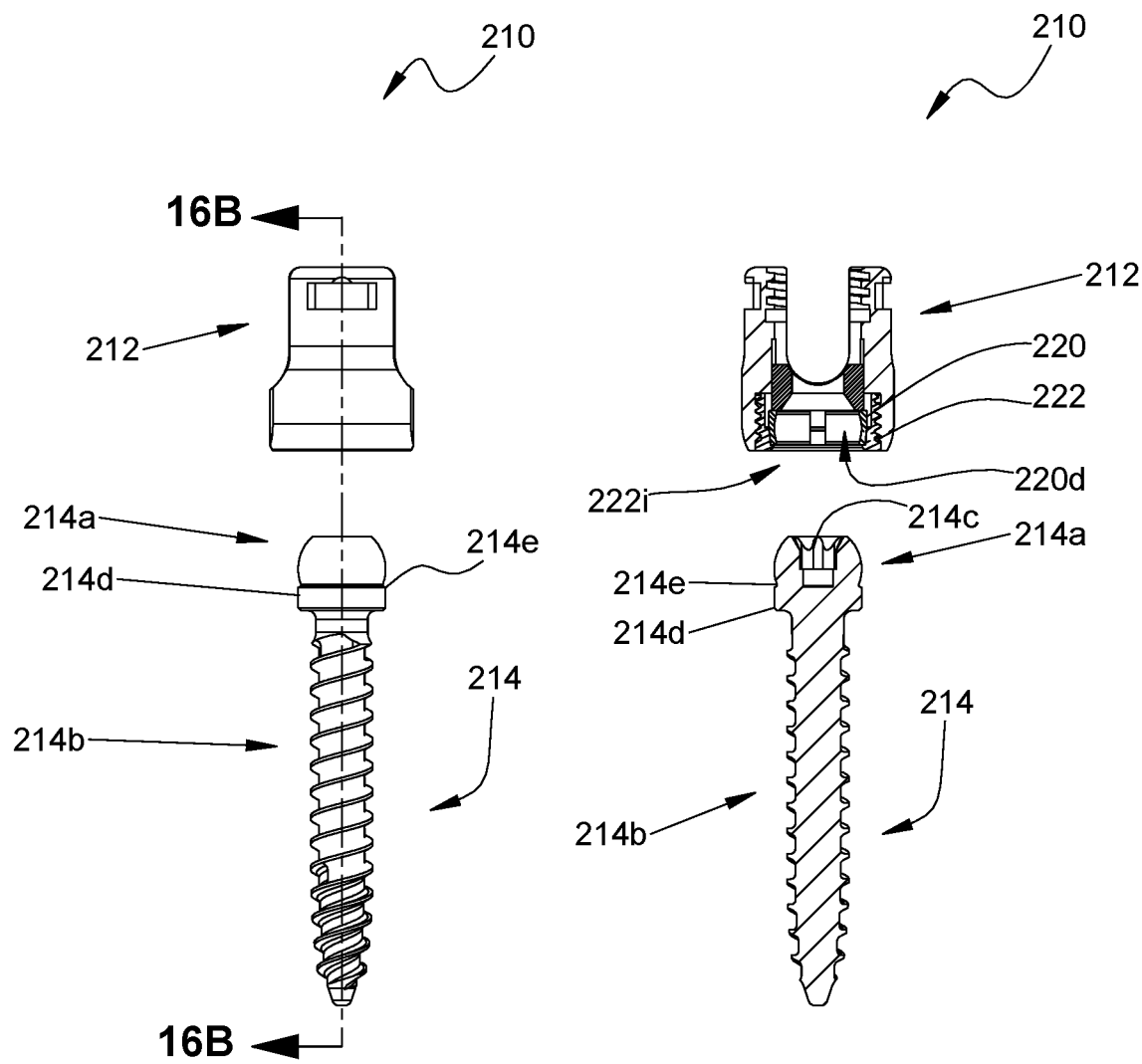
FIG. 16A is a front view of yet another embodiment of a spinal fixation device including a modular head assembly and a bone screw provided in accordance with the present disclosure.
FIG. 16B is a cross-sectional view of the spinal fixation device of FIG. 16A, taken along section-line 16B-16B of FIG. 16A.
Figure 17:
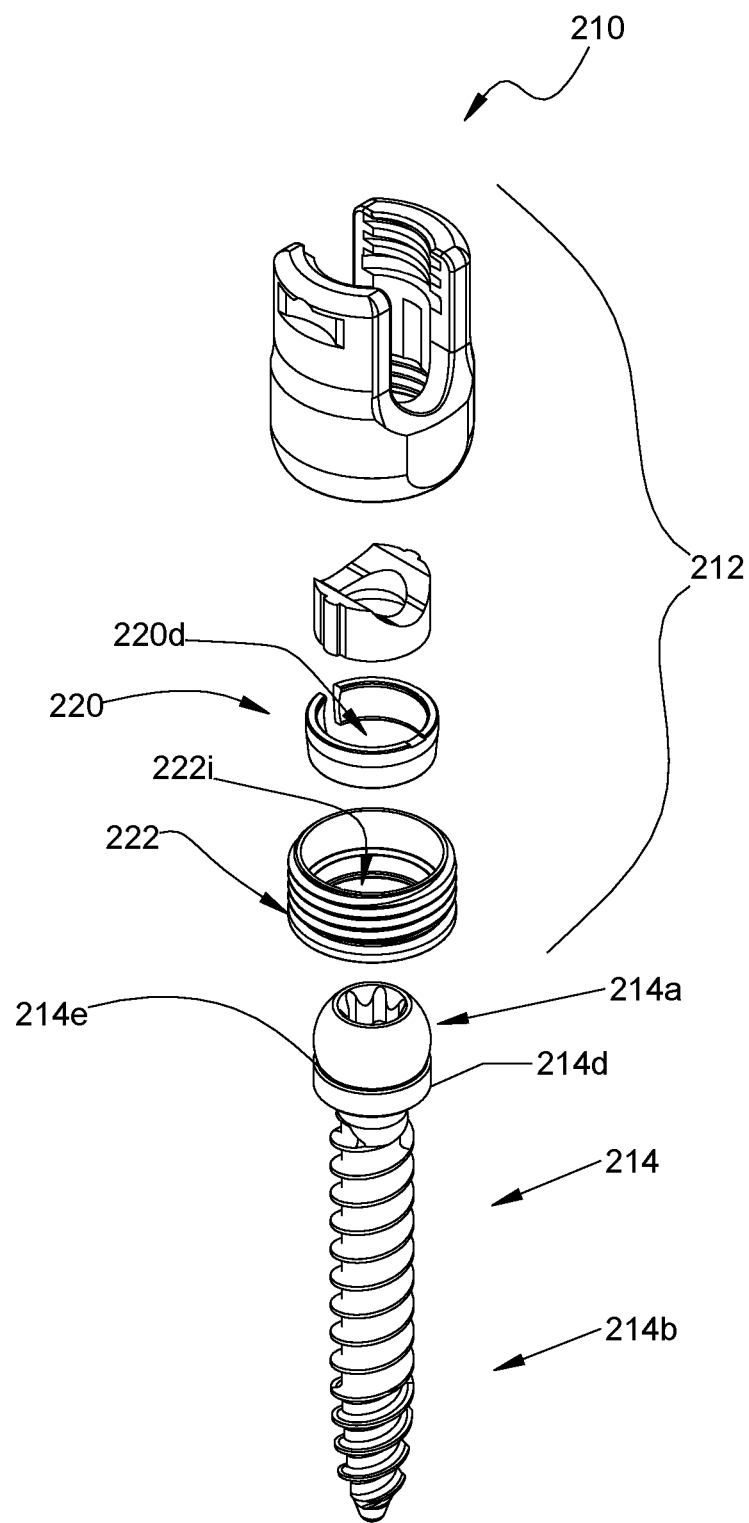
FIG. 17 is a perspective view of the spinal fixation device of FIG. 16A, shown with parts separated.

Turning now to FIGS. 16A, 16B, and 17, yet another embodiment of a spinal fixation device is illustrated and generally identified by reference numeral 210. The spinal fixation device 210 is substantially similar to the spinal fixation device 10, and therefore, only the differences therebetween will be described in detail hereinbelow in the interest of brevity.

The bone screw 214 is a mono-axial bone screw and includes a head 214a at a proximal end thereof and a threaded shank 214b extending distally therefrom. The head 214a includes a proximal end and a distal end and may define a generally spheroid configuration. The proximal end of the head 214a defines a tool engaging recess 214c that is configured to engage the engagement region 310 of the driver 300. As can be appreciated, the tool engaging recess may define any suitable shape capable of transmitting the rotational motion of the tool to the 214a of the bone screw 214, and in one non-limiting embodiment may define a hexalobe shape. The distal end of the head 214a defines a collar 214d having a proximal facing annular surface 214e that is configured to abut a portion of the snap ring 220 when the head 214a is captured therein, as will be described in further detail hereinbelow.

Assembly of the spinal fixation device 210 is substantially similar to that of the spinal fixation device 10 and therefore, only the differences therebetween will be described in detail hereinbelow in the interest of brevity. After the bone screw 214 has been secured into bone at the desired location, the modular head assembly 212 is advanced in a distal direction such that head 214a of the bone screw 214 is received within the bore 222i of the insert 222, and thereafter, within the lumen 220d of the snap ring 220. As the head 214a of the bone screw 214 advances within the lumen 220d of the snap ring 220 and is captured therein, the proximal facing annular surface 214e of the collar 214d of the bone screw 214 abuts a proximal surface of the snap ring 220 and inhibits radial movement of the bone screw 214 relative to the modular head assembly 212, but permitting axial rotation thereof relative to the modular head assembly 212 (e.g., about longitudinal axis C-C). In this manner, the bone screw 214 is constrained to movement in a single axis, and therefore is considered a mono-axial bone screw.

With reference to FIGS. 18A and 18B, a driver suitable for use with the spinal fixation device 10 is provided and generally identified by reference numeral 300. The driver includes an elongate shaft 302 having a proximal portion 304 and an opposed distal portion 306. The proximal portion 304 of the elongate shaft 302 defines a handle 308 that is configured to enable a clinician to selectively rotate the driver 300 (e.g., by gripping the handle 308 and applying rotational force thereto). The distal portion 306 of the driver 300 tapers to a driving but or a reduced diameter engagement region 310. The engagement region 310 includes protrusions 312 and recesses 314 that are complementary to the tool engaging recess 14g of the bone screw and the tool engaging recess 40a of the set screw 40. Once the engagement region 310 is inserted into the tool engaging recesses 14g or 40a, rotation of the driving tool 300 results in rotation of the bone screw 14 or the set screw 40. Thus, the driving tool 300 is capable of rotating the bone screw 14 and the set screw 40 for insertion or removal of the bone screw into bone and insertion or removal of the set screw 40 into the housing 16.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A spinal fixation device, comprising:
a modular head assembly, comprising:
a housing defining a proximal surface and an opposite, distal surface, the proximal and distal surfaces defining a throughbore therethrough;
an anvil configured to be slidably received within a portion of the throughbore;
an insert defining a proximal surface and an opposite, distal surface, the proximal surface defining a first counterbore therein terminating at a first annular surface, the first annular surface defining a second counterbore therein terminating at a second annular surface, the first counterbore having a first diameter and the second counterbore having a second diameter smaller than the first diameter;
a bone screw defining a head at a proximal portion thereof and a shank extending distally from the head;
a snap ring transitionable between a first configuration in which the snap ring is sized to receive the head of the bone screw and a second configuration in which the snap ring is compressed about the received head of the bone screw,
wherein movement of the snap ring from the first counterbore to the second counterbore compresses the snap ring from the first configuration to the second configuration and fixes the rotational and angular position of the bone screw relative to the housing.

2. The spinal fixation device according to claim 1, wherein the distal surface of the housing defines a third counterbore therein terminating at an annular face.

3. The spinal fixation device according to claim 2, wherein the annular face of the third counterbore defines a slot extending in a proximal direction, the slot extending through an inner surface of the throughbore.

4. The spinal fixation device according to claim 3, wherein the anvil defines a proximal surface and an opposite, distal surface, defining an outer surface extending therebetween, the outer surface defining a tab extending between the proximal and distal surfaces, the tab configured to be slidably received within the slot.

5. The spinal fixation device according to claim 4, wherein an inner surface of the third counterbore defines threads thereon.

6. The spinal fixation device according to claim 5, wherein the insert defines an outer surface extending between the proximal and distal surfaces, the outer surface defining threads thereon configured to threadably engage threads of the third counterbore.

7. The spinal fixation device according to claim 6, wherein the snap ring defines a proximal surface and an opposite, distal surface, the proximal and distal surfaces defining a lumen therethrough.

8. The spinal fixation device according to claim 7, wherein the proximal and distal surfaces of the snap ring define an outer surface extending therebetween, the outer surface defining a slot extending through the proximal and distal surfaces and being in open communication with the lumen.

9. The spinal fixation device according to claim 8, wherein the lumen of the snap ring defines a longitudinal axis extending along a centerline thereof, the lumen defining an inner surface having a concave profile extending along the longitudinal axis.

10. The spinal fixation device according to claim 9, wherein the snap ring is formed from a resilient material.

11. The spinal fixation device according to claim 10, wherein an intersection of the outer surface of the snap ring and the distal surface of the snap ring defines an undercut configured to abut a portion of the second counterbore of the insert.

12. A method of assembling a spinal fixation device, comprising:
assembling a modular head assembly, including:
advancing an anvil within a throughbore defined through a proximal and distal surface of a housing;
advancing a snap ring within a first counterbore defined through a proximal surface of an insert; and
rotating the insert in a first direction to threadably engage threads defined on an outer surface of the insert with threads defined on an inner surface of the housing until the insert is threadably coupled to the housing;
placing a bore defined through a distal surface of the insert adjacent a head of a bone screw; and
advancing the modular head assembly toward the head of the bone screw such that the head of the bone screw is received within the bore of the insert, and thereafter, within a lumen defined through distal and proximal surfaces of the snap ring to retain the head of the bone screw therein.

13. The method according to claim 12, wherein advancing the anvil within the throughbore of the housing includes advancing a tab defined on an outer surface of the anvil within a slot defined within an inner surface of the throughbore to inhibit rotation of the anvil relative to the housing.

14. The method according to claim 12, wherein advancing the head of the bone screw within the lumen of the snap ring includes advancing the head of the bone screw within the lumen of the snap ring such that a concave profile defined on an inner surface of the lumen engages the head of the bone screw to retain the head of the bone screw within the lumen.

15. The method according to claim 12, wherein advancing the head of the bone screw within the lumen of the snap ring includes the snap ring defining a slot extending through an outer surface thereof and extending through the proximal and distal surfaces, the slot enabling the snap ring to expand to a second, expanded state, as the head of the bone screw is received within the lumen, and return to a first, unexpanded state once the head of the bone screw is fully received within the lumen.

16. The method according to claim 12, further comprising advancing a spinal rod within a slot defined through an outer surface of the housing and extending through the proximal surface thereof.

17. The method according to claim 16, further comprising rotating a set screw in a first direction to threadably engage a plurality of threads defined on an outer surface of the set screw with a corresponding plurality of threads defined on an inner surface of the throughbore of the housing, wherein rotation of the set screw in the first direction causes the set screw to translate in a distal direction which causes a corresponding distal translation of the spinal rod, the anvil, and the snap ring.

18. The method according to claim 17, further including further rotating the set screw in the first direction to cause the snap ring to further translate in a distal direction and be received within a second counterbore defined through a first annular face defined by the first counterbore of the insert, wherein reception of the snap ring within the second counterbore causes the snap ring to compress around the head of the bone screw and lock the orientation of the bone screw relative to the modular head assembly.

19. A method of assembling a spinal fixation device, comprising:
advancing a bone screw within an incision formed in a patient's body;
driving the bone screw into a vertebra, the bone screw including a head at a proximal portion thereof and a threaded shank extending distally from the head;
assembling a modular head assembly, including:
advancing an anvil within a throughbore defined through a proximal and distal surface of a housing;
advancing a snap ring within a first counterbore defined through a proximal surface of an insert; and
rotating the insert in a first direction to threadably engage threads defined on an outer surface of the insert with threads defined on an inner surface of a second counterbore defined through the distal surface of the housing until the insert is threadably coupled to the housing;

advancing the modular head assembly into the incision;

placing a bore defined through a distal surface of the insert adjacent the head of the bone screw; and advancing the modular head assembly toward the head of the bone screw such that the head of the bone screw is received within the bore of the insert, and thereafter, within a lumen defined through distal and proximal surfaces of the snap ring to retain the head of the bone screw therein.

* * * * *